United States Patent [19]

Martin

[11] Patent Number: 5,788,683
[45] Date of Patent: Aug. 4, 1998

[54] SINUS ASPIRATION/IRRIGATION

[76] Inventor: Richard A. Martin, 17 Doctors' Park, Cape Girardeau, Mo. 63701

[21] Appl. No.: 216,543

[22] Filed: Mar. 23, 1994

[51] Int. Cl.$^6$ ............................. A61M 1/00; A61C 17/06
[52] U.S. Cl. .............................................. 604/319; 604/74
[58] Field of Search .................................. 604/316, 317, 604/318, 319, 73, 74, 75, 76, 36, 19

[56] References Cited

U.S. PATENT DOCUMENTS

| | | | |
|---|---|---|---|
| 356,206 | 1/1887 | Van Altena et al. | 604/78 |
| 790,051 | 5/1905 | Halstead | 604/74 |
| 2,208,089 | 7/1940 | Von Grolman | 604/75 |
| 2,883,983 | 4/1959 | Biederman | 604/73 |
| 3,603,366 | 9/1971 | Albizati | 604/317 |
| 3,738,363 | 6/1973 | Lunas et al. | 604/76 |
| 3,855,997 | 12/1974 | Sauer | 604/319 |
| 4,195,633 | 4/1980 | Nehring | 604/318 |
| 4,263,912 | 4/1981 | Adams | 604/75 |
| 4,403,611 | 9/1983 | Babbitt et al. | |
| 4,764,167 | 8/1988 | Tu | |
| 4,828,546 | 5/1989 | McNeil et al. | 604/319 |
| 4,925,447 | 5/1990 | Rosenblatt | 604/319 |
| 5,073,172 | 12/1991 | Fell | 604/319 |
| 5,098,418 | 3/1992 | Maitz et al. | 604/319 |
| 5,114,415 | 5/1992 | Shedlock | 604/319 |
| 5,183,467 | 2/1993 | Mouney | |
| 5,185,007 | 2/1993 | Middaugh | 604/319 |

OTHER PUBLICATIONS

Exhibit A, H.S. Martin & Son, Inc, 1971, copy of record (submitted by applicant).

*Primary Examiner*—Paul J. Hirsch
*Attorney, Agent, or Firm*—Nixon & Vanderhye P.C.

[57] ABSTRACT

A nasal aspirator/irrigation device can be used in a method of obtaining human mucopurulence suited for culturing to determine the type of pathogens contained in it. The aspirator includes a hollow body having a top portion and a bottom portion, a hollow capture chamber connected to the bottom portion, a nasal conduit connected to the body top portion having a free end dimensioned to fit into a human nostril, and a vacuum control conduit which extends upwardly from the body top portion. The free end has a hollow triangular prism shape adapted to provide a good fit in a human nostril, and the capture chamber is releasably connected, such as by screw-threads, so that it can be detached, sealed, and shipped to a diagnostic site. The capture chamber may include culture media in it prior to utilization. Sterile liquid is introduced into a first of the patient's nostrils, the aspirator device—connected to vacuum—introduced into the other nostril. The recaptured liquid and entrained mucopurulence is placed in the sealed container and transported to a pathogen-diagnostic site.

20 Claims, 3 Drawing Sheets

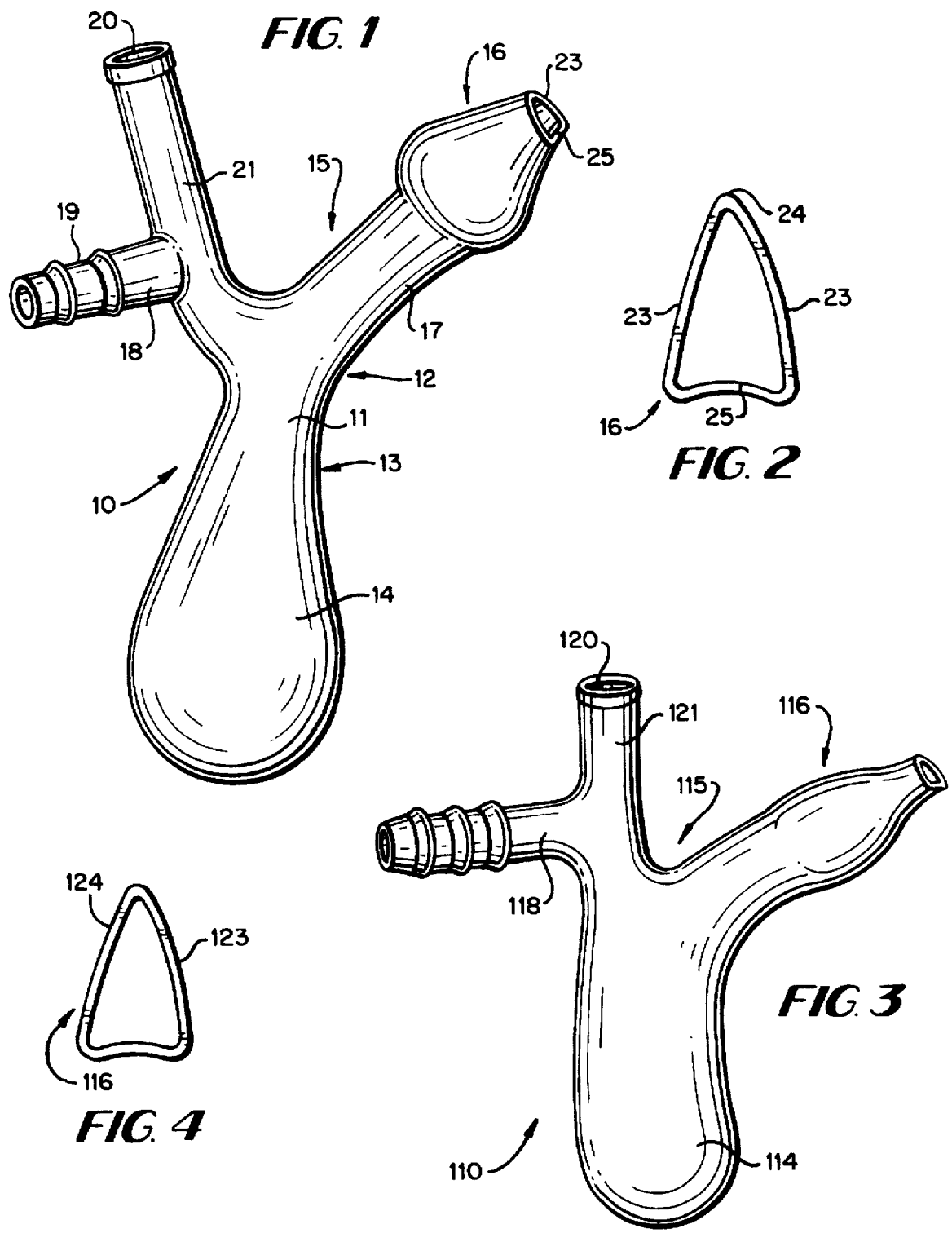

SINUS ASPIRATION/IRRIGATION

BACKGROUND AND SUMMARY OF THE INVENTION

The invention relates to a method of obtaining human mucopurulence of pathogens contained therein, and an irrigation device which can be simply and effectively used not only to obtain human mucopurulence for culturing, but also to "clean up" sinuses pre-operatively, or post-operatively.

Historically, numerous methods of sinus aspiration/irrigation have been used. Maxillary antral puncture [transantral trocar (medical and anterior) and direct cannulation] have been the most effective therapeutically. Transantral aspiration (medical and anterior) is the diagnostic "gold standard" for gram stain and culture and sensitivity. Nasal smears have lacked correlation in many studies although some studies suggest carefully selected nasal smears from the middle meatus may be helpful diagnostically, but are of little therapeutic value.

Needle aspiration and irrigation are most helpful both diagnostically and therapeutically. However, this is rarely performed on children without anesthesia and carry some risk of mucoperiosteal inflammation. It can be associated with significant nosebleeds and can be stressful even for the adult. This therapy is also limited to the maxillary sinus.

The saline aspiration/irrigation technique according to the present invention is painless, economical, and versatile—it can be performed on patients of all ages, both diagnostically and therapeutically. Its success is based upon Bernoulli's principle and the Venturi effect.

According to one aspect of the present invention, a method of obtaining human mucopurulence suitable for culturing to determine the type of pathogens contained therein is provided. The method utilizes an aspirator comprising a nasal conduit, a vacuum-connected conduit, a vacuum control opening, and a capture chamber all connected to a common body. The method comprises the following steps: (a) With a human patient upright, introducing at least about 50 ml of sterile liquid into a first of the patient's nostrils. (b) Substantially simultaneously with step (a) inserting the nasal conduit of the aspirator into the second of the patient's nostrils while the vacuum connected conduit is connected to a source of vacuum. (c) Covering or uncovering the vacuum control opening to provide the desired level and timing of vacuum to suck material including the sterile liquid introduced in step (a), with any mucopurulence it entrains, into the capture chamber. (d) Determining if the material sucked into the capture chamber in the practice of steps (a)–(c) contains a sufficient amount and quality of mucopurulence suitable for culturing. (e) If the material from step (d) is suitable for culturing, providing the material in a sealed container suitable for transport to a pathogen diagnostic site. And, (f) if the material from step (d) is not suitable for culturing, discharging the material from the capture chamber, and repeating steps (a)–(d) until material suitable for culturing is captured in the capture chamber, and then practicing step (e).

Step (a) is typically practiced by introducing saline using an asepto syringe while the patient says "K", "K", "K", or—if an infant or small child—simply cries. Preferably the capture chamber is releasably connected to the body of the aspirator, in which case step (e) is practiced by disconnecting the capture chamber from the body of the aspirator, and covering the top of the capture chamber so that the material will not inadvertently escape the capture chamber. There is also the further step, after step (e), of replacing the capture chamber with another, clean capture chamber, so that a different capture chamber is provided for the next patient. The releasable connection between the capture chamber and the body of the aspirator may be a screw-threaded connection, in which case step (e) is practiced by unscrewing the capture chamber from the body, and then screwing a cap onto the capture chamber. Culture media may be placed in the capture chamber prior to step (e). After step (e) there is the further step (typically at a diagnostic lab) of culturing the mucopurulence and analyzing the cultured mucopurulence to determine what pathogens it contains.

Step (f) is typically practiced by withdrawing the nasal conduit from the second nostril, and tipping the aspirator so that the material in the capture chamber flows out of the chamber into a waste receptacle.

The invention also comprises a nasal aspirator/irrigation device which not only can be used in the diagnostic procedure described above, but also can be used for irrigation, either to relieve pain, to pre-operatively clean out the sinuses, or to post-operatively (typically after sinus surgery) clean out the sinuses.

The nasal aspirator/irrigation device according to the invention comprises the following elements: A hollow body having a top portion and a bottom portion opposite the top portion. A hollow capture chamber connected to the body bottom portion, and having a volume of at least about 50 ml. A nasal conduit connected to the body top portion, having a free end portion dimensioned to fit into a human nostril. A vacuum-connection conduit connected to the body top portion remote from the nasal conduit, and a vacuum-control opening operatively defined in the body top portion, remote from the nasal conduit. The device is dimensioned to fit in an adult human hand, and, the nasal conduit free end has the general configuration of a hollow triangular prism and provides a comfortable, sealed, fit of the nasal conduit in a human nostril.

All of the components of the device typically are of transparent plastic, although under some circumstances they could be made of other material such as glass, and could be opaque.

The device typically further comprises a vacuum control conduit extending upwardly from the body top portion, opposite the capture chamber, and the vacuum-control opening is provided in a portion of the vacuum-control conduit most remote from the body. The vacuum control conduit and nasal conduit are typically in a common plane and make an angle of about 60°–100° with respect to each other, and the vacuum-connection conduit is also preferably co-planar with the vacuum-control conduit and the nasal conduit and makes an angle of about 60°–130° with respect to the vacuum-control conduit. The nasal conduit typically includes an enlarged bulbous portion between the free end thereof and the body.

The device also preferably comprises means for releasably connecting the capture chamber to the body so that the capture chamber is sealed to the body and readily detached therefrom and has an open, readily sealed, top length attached. The releasably connecting means may comprise mating screw threads on the body in the capture chamber, although almost any other conventional connection between two hollow components that will provide a sealed connection may be provided including an interference or friction fit (typically with resilient materials), a bayonet-type connection, or the like.

It is the primary object of the present invention to provide an improved method of obtaining human mucopurulence suitable for culturing, and an improved nasal aspirator/ irrigation device. This and other objects of the invention will become clear from an inspection of the detailed description of the invention and from the appended claims.

BRIEF DESCRIPTION OF THE DRAWINGS

FIG. 1 is an isometric view of an adult size of an exemplary nasal aspirator/irrigation device (shown to actual scale) according to the present invention;

FIG. 2 is an end view of only the nasal conduit free end of the device of FIG. 1;

FIGS. 3 and 4 are views like those of FIGS. 1 and 2 only for a pediatric size of nasal aspirator/irrigation device according to the present invention;

DETAILED DESCRIPTION OF THE DRAWINGS

Figure 5:
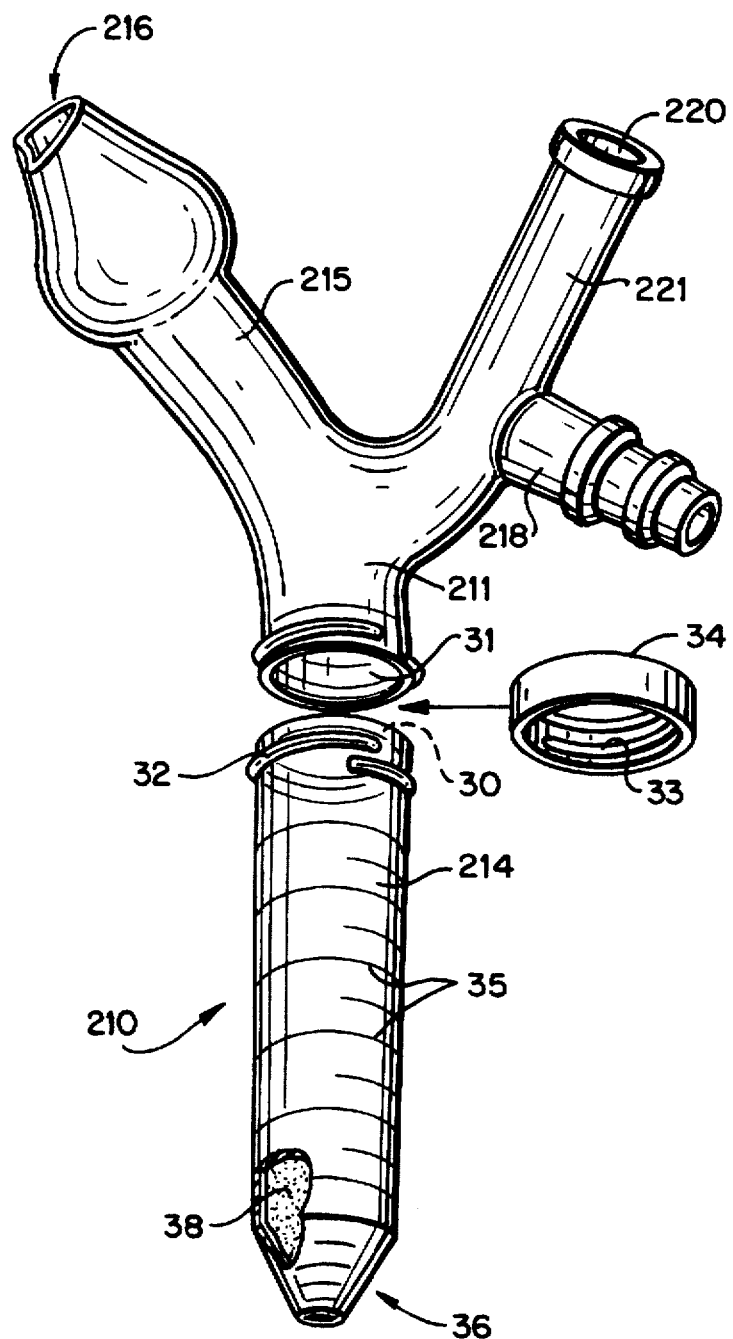
FIG. 5 is an isometric view of another modification of an aspirator/irrigation device according to the present invention shown with a detachable capture chamber, and also illustrating a cap that can be used with the capture chamber to seal it once it is detached from the rest of the device.

FIGS. 1 and 2 illustrate an exemplary aspirator/irrigation device according to the present invention, shown generally by reference numeral 10 in FIG. 1. The device 10 includes a hollow body 11 having a top portion 12 and a bottom portion 13 opposite the top portion 12. A hollow capture chamber 14 preferably having a volume of at least about 50 ml is connected to the bottom portion 13 of the body 11. In FIG. 1 this connection is an integral connection, the body 11 and the capture chamber 14 being made integrally of a single piece of material.

The device 10 also includes a nasal conduit or nozzle 15 connected to the body 11 top portion 12, and having a free end portion 16 dimensioned to fit into a human nostril, in this case an adult nostril. Typically there is an enlarged bulbous portion 17 between the free end 16 and the body 11 formed in the nasal conduit 15.

The device 10 further comprises a vacuum connection conduit 18 operatively connected to the body 11 top portion 12, and being connectable up to a source of vacuum, such as a vacuum pump. The conduit 18 typically includes surface manifestations 19 which facilitate sealed connection thereof to a rubber or plastic hose which leads from the device 10 to the vacuum source.

The device 10 further includes a vacuum control opening 20 operatively defined in the body 11 top part 12. Preferably—as illustrated in FIG. 1—the opening 20 is defined at a free end of a vacuum control conduit 21, which free end is the portion thereof most remote from the body 11. As illustrated in FIG. 1, preferably the nasal conduit 15, vacuum-connection conduit 18, and vacuum-control conduit 21 are all integral with each other and with the body 11, made of the same piece of material. The device 10—shown to actual scale in FIG. 1—is dimensioned to fit in a normal size adult human hand. All of the conduits 15, 18, and 21 are preferably co-planar, with the conduits 15, 21 making an angle that is preferably about 60°–110° with respect to each other (an angle of about 80° as shown in FIG. 1), while the conduits 21, 18 make an angle of about 60°–130° with respect to each other (an angle of about 70° is seen in FIG. 1).

What has been described heretofore is known per se, simulating a transparent glass device of approximately 1970 vintage believed to have been made by H. S. Martin & Son Inc. of Evanston, Ill., designed use unknown. According to the present invention, however, the free end 16 of the nasal conduit 15 is constructed in a way such that it fits more appropriately into the vestibule of the human nose, providing a comfortable, sealed fit of the nasal conduit in a human nostril. The particular nasal conduit free end 16 construction illustrated in FIGS. 1 and 2 allows a greater area of negative pressure to be generated in the area of the valve region of the nose, and allows a better and more comfortable fit into the nose than the H. S. Martin structure. As seen in FIGS. 1 and 2, the free end 16 preferably has a configuration of a hollow triangular prism, having sides 23 which taper to a rounded point 24, and a base 25. The hollow triangular prism preferably comprises an isosceles triangle, FIG. 1 illustrating the preferred actual size, and FIG. 2 showing the angular relationships between the components preferred in the adult nasal aspirator/irrigation device 10 in enlarged scale.

Also, the device 10 according to the invention,—as distinct from the H. S. Martin & Son device—preferably is made of transparent plastic, of the conventional types used in medical applications, i.e. that will not degenerate when exposed to human fluids, may be sterilized, and will not break if dropped.

The modification illustrated in FIGS. 3 and 4—also shown at actual size in FIG. 3—is essentially identical as far as functionality is concerned to the embodiment of FIG. 1, the only significant difference being the size. In the FIGS. 3 and 4 embodiment components comparable to those in the FIGS. 1 and 2 embodiment are shown by the same reference numeral only preceded by a "1".

The primary difference between the device 10 and the device 110 is that the capture chamber 114 of the device 110 is slightly smaller than the capture chamber 14. Also the free end 116 of the nasal conduit 115 is slightly smaller, to take into account the smaller size of a child's nostril.

The device of FIG. 5 is substantially identical to the device of FIG. 1 except for the connection between the capture chamber and main body thereof. In the FIG. 5 embodiment structures comparable to those in the FIG. 1 embodiment are shown by the same two digit reference numeral, only preceded by a "2".

The only difference between the FIG. 5 and FIG. 1 embodiment is that body 211 and the capture chamber 214 are not formed of the same integral structure, but rather means are provided for readily releasably connecting the capture chamber 214 to the body 11 so that the capture chamber 214 is sealed to the body 211, and when readily detached therefrom has an open, readily sealable top 30. While the means for releasably connecting the capture chamber 214 and the body 211 may comprise almost any conventional structure for connecting two hollow components together in a sealed manner, such as bayonet couplings, interference or friction fit, etc., in the preferred embodiment illustrated in FIG. 1 the releasable connecting means comprise screw threads 31 on the body 211 and cooperating, mating, screw threads 32 on the capture chamber 214. Preferably the screw threads 31 are internal screw threads, while the screw threads 32 are external of the capture chamber 214. The screw threads 32 also are adapted to mate with the internal screw threads 33 of a cap 34 which can be screwed onto the open top 30 of the capture chamber 214 to seal it tightly so that no fluid can leak therefrom.

For ease of construction, and also to make the device as inexpensive as possible, it is preferred that the capture chamber 214 merely be an already existing container typically used in medical practices, and it may include volume marks (a scale) 35 thereon. The bottom 36 thereof may have a conical taper as illustrated, or be flat. The chamber 214 also is preferably made of transparent plastic.

The construction illustrated in FIG. 5 has a number of advantages. Probably the most significant advantage is that it allows ready transport of collected mucopurulence to be sent to a laboratory for culturing of the mucopurulence to determine the type of pathogens contained therein. The structure 210 also minimizes the chance of contamination of a mucopurulence sample from one patient to the next since a new capture chamber 214 is put into place, and the structure 210 also facilitates sterilization of all of the components since detachment of the capture chamber 214 makes sterilization of the interior of the body 211, and conduits 215, 218 and 221 easier since it is much simpler to introduce sterilizing fluid into contact with the interior surfaces thereof.

It may be desirable under some circumstances to provide a culture media in the capture chamber 214 itself so that culturing can be initiated even while the capture chamber 214 (with the cap 34 thereon) is being transferred to a diagnostic laboratory. FIG. 5 schematically illustrates culture media 38 in the chamber 214. The culture media 38 is illustrated in a gel form adhered to the interior of the capture chamber 214, but a wide variety of other forms can also be utilized, such as conventional capsules that break and soak cotton to provide a substrate for release of the culture media into the interior volume of the capture chamber 214.

Figure 6:
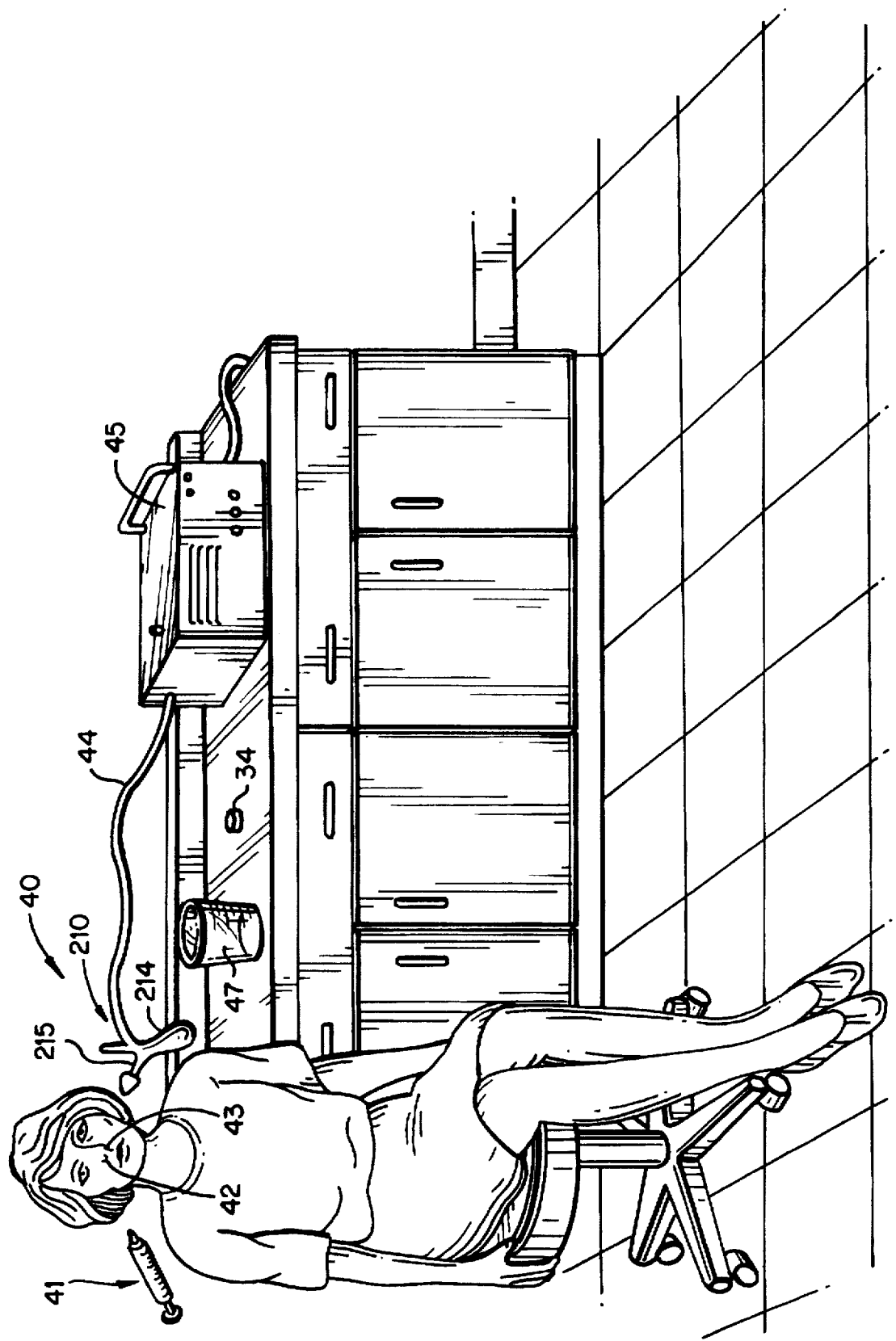
FIG. 6 is a schematic view illustrating utilization of the device of FIG. 5 for performing a procedure of obtaining human mucopurulence suitable for culturing to determine the type of pathogens contained therein.

FIG. 6 schematically illustrates a preferred use of the device 210 (the use of the devices 10, 110 being comparable) for obtaining human mucopurulence suitable for culturing. It should be understood, however, that the devices 10, 110, 210 can also be used for irrigation, being used for irrigation in the same manner as the method described hereinafter except that when performing an irrigation procedure the fluid discharged into the capture chamber 14, 114, 214 is merely discarded.

The patient 40 is in the upright position, either sitting or standing, therefore contamination of an infected sinus is unlikely. Using an asepto syringe 41 or the like, a medically trained technician (such as a doctor or a nurse) introduces at least about 50 ml of sterile liquid (such as saline) into the patient's first nostril 42. Substantially simultaneously with the introduction of the saline the technician inserts the free end 216 of the nasal conduit 215 of the device 210 into the second nostril 43. The device 210 is connected up by a vacuum hose 44 (connected to vacuum-connection conduit 218) to a source of vacuum such as a conventional vacuum pump 45. By covering or uncovering (partially or completely) the vacuum control opening 220 in the device 210 with a finger, the technician provides a desired level of vacuum to suck (without hurting the patient 40) material, including the saline introduced by the syringe 41, with any mucopurulence it entrains, into the capture chamber 214. The volume of the capture chamber 214 is sufficient to accommodate the entire volume of the syringe 41, as well as a significant amount of mucopurulence.

By observing the material collected in the capture chamber 214 (since it is transparent this is a simple task) the technician determines if the material sucked into the capture chamber 214 contains a sufficient amount and quality of mucopurulence to be suitable for culturing. If the amount and quality are suitable, the vacuum pump 45 is turned off, the capture chamber 214 is unscrewed from the body 211, and the cap 34 screwed onto the capture chamber 214. The sealed capture chamber 214 is then shipped to a diagnostic lab where the pathogens in the mucopurulence are evaluated by culturing using conventional techniques. Depending upon the pathogens that exist—such as B Beta strep group A, staph aureus, pseudomonas aeruginosa, or the like—a correct antibiotic prescription, and/or other treatment, can be effected.

If the material sucked into the capture chamber 214 is not suitable for culturing, the material is discharged from the capture chamber 214 and the previous steps of introduction of sterile liquid, withdrawal, and the like, are practiced again until a suitable amount and quality of mucopurulence is obtained. Discharge of material from the chamber 214 may be practiced either by disconnecting it and pouring it into a waste receptacle 47, or preferably merely by tilting the device 210 so that the fluid in the chamber 214 merely flows out of the nasal conduit 215 into the waste receptacle 47.

The technician typically can practice the procedure by himself or herself, the syringe 41 being held in one hand while the device 210 is simultaneously held in the other. The opening 220 can be covered by his or her finger or thumb substantially simultaneously with (e.g. simultaneously or slightly after) introduction of the saline with syringe 41.

It will thus be seen that according to the present invention a method and apparatus have been provided which are simple, economical, and effective, as well as versatile. While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent methods and devices.

What is claimed is:

1. A method of obtaining human mucopurulence suitable for culturing to determine the type of pathogens contained therein, utilizing an aspirator comprising a nasal conduit, a vacuum-connected conduit, a vacuum control opening, and a capture chamber all connected to a common body, comprising the steps of:

(a) with a human patient upright, introducing at least about 50 ml of sterile liquid into a first of the patient's nostrils;

(b) substantially simultaneously with step (a) inserting the nasal conduit of the aspirator into the second of the patient's nostrils while the vacuum connected conduit is connected to a source of vacuum;

(c) covering or uncovering the vacuum control opening to provide the desired level and timing of vacuum to suck material including the sterile liquid introduced in step (a), with any mucopurulence it entrains, into the capture chamber;

(d) determining if the material sucked into the capture chamber in the practice of steps (a)–(c) contains a sufficient amount and quality of mucopurulence suitable for culturing;

(e) if the material from step (d) is suitable for culturing, providing the material in a sealed container suitable for transport to a pathogen diagnostic site; and (f) if the material from step (d) is not suitable for culturing, discharging the material from the capture chamber, and repeating steps (a)–(d) until material suitable for culturing is captured in the capture chamber, and then practicing step (e).

2. A method as recited in claim 1 wherein the capture chamber is releasably connected to the body of the aspirator, and wherein step (e) is practiced by disconnecting the capture chamber from the body of the aspirator, and covering the top of the capture chamber so that the material will not inadvertently escape the capture chamber.

3. A method as recited in claim 2 comprising the further step, after step (e), of replacing the capture chamber with another, clean capture chamber, so that a different capture chamber is provided for the next patient.

4. A method as recited in claim 2 wherein the releasable connection between the capture chamber and the body of the aspirator is a screw-threaded connection, and wherein step (e) is practiced by unscrewing the capture chamber from the body, and then screwing a cap onto the capture chamber.

5. A method as recited in claim 2 comprising the further step of placing culture media in the capture chamber prior to step (e), and comprising the further step, after step (e), of culturing the mucopurulence and analyzing the cultured mucopurulence to determine what pathogens it contains.

6. A method as recited in claim 1 wherein step (a) is practiced by introducing saline using an asepto syringe while the patient says "K", "K", "K", or cries.

7. A method as recited in claim 1 wherein step (f) is practiced by withdrawing the nasal conduit from the second nostril, and tipping the aspirator so that the material in the capture chamber flows out of the chamber into a waste receptacle.

8. A nasal aspirator/irrigation device comprising:

a hollow body having a top portion and a bottom portion opposite said top portion; a hollow capture chamber connected to said body bottom portion; a nasal conduit connected to said body top portion, having a free end portion dimensioned to fit into a human nostril; a vacuum-connection conduit connected to said body top portion remote from said nasal conduit; a vacuum-control opening operatively defined in said body top portion, remote from said nasal conduit; said device being dimensioned to fit in an adult human hand; and wherein said nasal conduit free end has the general configuration of a hollow triangular prism and provides a comfortable, sealed, fit of said nasal conduit in a human nostril.

9. A device as recited in claim 8 wherein all of said body, nasal conduit, vacuum-connection conduit, and capture chamber are of transparent plastic.

10. A device as recited in claim 9 further comprising a vacuum control conduit extending upwardly from said body top portion, opposite said capture chamber; and wherein said vacuum-control opening is provided in a portion of said vacuum control conduit most remote from said body.

11. A device as recited in claim 10 wherein said vacuum control conduit and nasal conduit are in a common plane, and make an angle of about 60–110 degrees with respect to each other.

12. A device as recited in claim 11 wherein said vacuum-connection conduit is in the same plane as said vacuum control conduit and nasal conduit, and makes an angle of about 60–130 degrees with respect to said vacuum control conduit.

13. A device as recited in claim 8 further comprising means for releasably connecting said capture chamber to said body so that said capture chamber is sealed to said body, and readily detached therefrom and has an open, readily sealed, top when detached.

14. A device as recited in claim 13 wherein said releasably connecting means comprise mating screw threads on said body and said capture chamber; and further comprising a cap with screw-threads mating with said capture chamber for sealing said open top of said capture chamber when detached from said body.

15. A device as recited in claim 13 wherein all of said body, nasal conduit, vacuum-connection conduit, and capture chamber are of transparent plastic, and wherein said capture chamber includes culture media therein prior to utilization of said device.

16. A device as recited in claim 8 wherein said nasal conduit includes an enlarged bulbous portion between said free end thereof and said body, and wherein said chamber has a volume of at least about 50 ml.

17. A nasal aspirator/irrigation device comprising:

a hollow body having a top portion and a bottom portion opposite said top portion; a hollow capture chamber connected to said body bottom portion, and having a volume of at least about 50 ml; a nasal conduit connected to said body top portion, having a free end portion dimensioned to fit into a human nostril; a vacuum-connection conduit connected to said body top portion remote from said nasal conduit; a vacuum-control opening operatively defined in said body top portion, remote from said nasal conduit; said device being dimensioned to fit in an adult human hand;

means for releasably connecting said capture chamber to said body so that said capture chamber is sealed to said body, and readily detached therefrom and has an open, readily sealed, top when detached and wherein said capture chamber includes culture media therein prior to utilization of said device.

18. A device as recited in claim 17 wherein said releasably connecting means comprise mating screw threads on said body and said capture chamber; and further comprising a cap with screw-threads mating with said capture chamber for sealing said open top of said capture chamber when detached from said body.

19. A device as recited in claim 17 wherein all of said body, nasal conduit, vacuum-connection conduit.

20. A device as recited in claim 17 further comprising a vacuum control conduit extending upwardly from said body top portion, opposite said capture chamber; wherein said vacuum-control opening is provided in the most remote portion of said vacuum control conduit; wherein said vacuum control conduit and nasal conduit are in a common plane, and make an angle of about 60–110 degrees with respect to each other; and wherein said nasal conduit includes an enlarged bulbous portion between said free end thereof and said body.

* * * * *